United States Patent [19]
Stone et al.

[11] Patent Number: 5,602,185
[45] Date of Patent: Feb. 11, 1997

[54] SUBSTITUTED TRIFLUOROSTYRENE COMPOSITIONS

[75] Inventors: Charles Stone, Vancouver; Alfred E. Steck, West Vancouver; Robert D. Lousenberg, North Vancouver, all of Canada

[73] Assignee: Ballard Power Systems Inc., Burnaby, Canada

[21] Appl. No.: 480,098

[22] Filed: Jun. 6, 1995

Related U.S. Application Data

[63] Continuation-in-part of Ser. No. 124,924, Sep. 21, 1993, Pat. No. 5,422,411.

[51] Int. Cl.$^6$ ............................. C08J 5/22; C08F 14/18
[52] U.S. Cl. ............................. 521/27; 521/32; 521/33; 521/31; 526/242; 526/243; 526/247; 526/248; 526/249; 526/278; 526/286; 526/287; 526/291; 526/292.8; 526/292.9; 562/826; 429/29
[58] Field of Search ............................. 526/243; 521/37, 521/31, 27; 562/826

[56] References Cited

U.S. PATENT DOCUMENTS

| | | |
|---|---|---|
| 2,651,627 | 9/1953 | Prober . |
| 3,226,361 | 12/1965 | Borman . |
| 3,282,875 | 11/1966 | Connolly et al. . |
| 3,341,366 | 9/1967 | Hodgdon, Jr. et al. . |
| 3,528,858 | 9/1970 | Hodgdon, Jr. et al. . |
| 3,560,568 | 2/1971 | Resnick . |
| 4,012,303 | 3/1977 | D'Agostino et al. . |
| 4,090,931 | 5/1978 | Motani ........................... 204/98 |
| 4,330,654 | 5/1982 | Ezell et al. . |
| 4,605,685 | 8/1986 | Momose et al. . |
| 5,422,411 | 6/1995 | Wei ............................. 526/243 |

FOREIGN PATENT DOCUMENTS

| | | |
|---|---|---|
| 53-26884 | 3/1978 | Japan . |
| 3-27053 | 2/1991 | Japan . |

OTHER PUBLICATIONS

"Palladium–Catalyzed Cross–Coupling of Perfluoroalkenylzine Reagents with Aryl Iodides, A New, Simple Synthesis of α,β,β–Trifluorostyrenes and the Stereoselective Preparation of 1–Arylperfluoropropenes", *J. Org. Chem.*, vol. 53, pp. 2714–2720, Heinze et al., 1988.

"α,β,β–Trifluorostyrene and polymers based on it", *Russian Chemical Reviews*, vol. 59, pp. 575–589, Nikitina, 1990.

"The Spin Delocalization Substitutent Parameter $\sigma_{jj}$.5. Correlation Analysis of $^{19}F$ Chemical Shifts Of Substituted Trifluorostyrenes. The Unresolved Polar Substitutent Parameter $\sigma_{mb}$", *Journal of Physical Organic Chemistry*, vol. 3, pp. 643–650, Ji et al, 1990.

"Variation of Transfer Coefficient in Electrochemical Correlations of ρσ Type. Reduction of Aromatic Sulfonyl Fluorides on Mercury Electroce", *Polish Journal of Chemistry*, vol. 66, pp. 101–110, Sanecki, 1992.

PCT/International Publication No. WO 95/08581, Wei et al, Mar. 30, 1995.

*Primary Examiner*—Fred Zitomer
*Attorney, Agent, or Firm*—McAndrews, Held & Malloy, Ltd.

[57] ABSTRACT

Sulfonyl fluoride substituted α,β,β-trifluorostyrene monomers are disclosed. The monomers are incorporated into polymeric compositions which are conveniently hydrolyzed to produce polymeric compositions which include ion-exchange moieties. The resulting compositions which include ion-exchange moieties are particularly suitable for use as solid polymer electrolytes in electrochemical applications, such as, for example, electrochemical fuel cells.

45 Claims, No Drawings

SUBSTITUTED TRIFLUOROSTYRENE COMPOSITIONS

CROSS-REFERENCE TO RELATED APPLICATION

This application is a continuation-in-part of U.S. patent application Ser. No. 08/124,924 filed Sep. 21, 1993, now U.S. Pat. No. 5,422,411 issued Jun. 6, 1995, entitled "Trifluorostyrene And Substituted Trifluorostyrene Copolymeric Compositions and Ion-exchange Membranes Formed Therefrom". The related application, incorporated herein by reference in its entirety, describes polymeric compositions derived from copolymers of α,β,β-trifluorostyrene with a variety of substituted α,β,β-trifluorostyrenes. These compositions are suitable for use as, for example, membranes, particularly as ion-exchange membranes.

FIELD OF THE INVENTION

The present invention relates to polymeric compositions derived from copolymers of α,β,β-trifluorostyrene with a variety of substituted α,β,β-trifluorostyrenes. More particularly, the present invention relates to copolymers of α,β,β-trifluorostyrene and substituted β,β,β-trifluorostyrenes including sulfonyl fluoride substituted α,β,β-trifluorostyrene monomers. These copolymers are conveniently hydrolyzed to give polymeric compositions with ion-exchange moieties. The resulting polymeric compositions which include ion-exchange moieties are particularly suitable for use as solid polymer electrolytes in electrochemical applications, such as, for example, electrochemical fuel cells.

BACKGROUND OF THE INVENTION

Polymeric compositions, derived from copolymers of α,β,β-trifluorostyrene with a variety of substituted α,β,β-trifluorostyrenes, in which at least one of the substituents is an ion-exchange moiety have utility as ion-exchange membranes, as disclosed in related U.S. Pat. No. 5,422,411 issued Jun. 6, 1995.

Typically, ion-exchange moieties are introduced into copolymers containing unsubstituted α,β,β-trifluorostyrene units (so called "base copolymers") via aromatic substitution of at least a portion of those units. This typically involves preparation and purification of the base copolymer, followed by aromatic substitution and subsequent isolation and purification of copolymer containing the ion-exchange moiety. In an alternative approach for introducing ion-exchange functionality, an ion-exchange moiety or masked ion-exchange moiety is present in one or more of the monomers prior to copolymerization. The use of a masked ion-exchange moiety, which can be converted to the corresponding ion-exchange moiety via a simple procedure, can be advantageous.

SUMMARY OF THE INVENTION

Polymeric compositions of the present invention include:

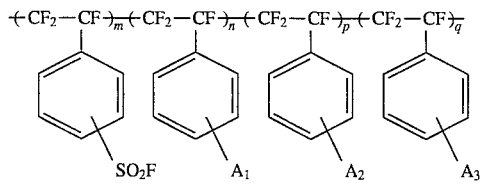

where m is an integer greater than zero, and n, p and q are zero or an integer greater than zero; $A_1$, $A_2$ and $A_3$ are selected from the group consisting of hydrogen, halogens, alkyls, perfluoroalkyls, CF=$CF_2$, CN, $NO_2$, OH, O—R (where R is selected from the group consisting of alkyls, perfluoroalkyls and aryls).

The above polymeric compositions are prepared by polymerization (where only m is an integer greater than zero) or copolymerization (where m is an integer greater than zero and at least one of n, p and q is an integer greater than zero) of monomer isomers having the chemical formula:

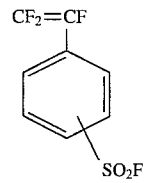

The sulfonyl fluoride moiety (—$SO_2F$) can be converted to a sulfonic acid (—$SO_3H$) moiety by conventional techniques such as, for example, hydrolysis. The $A_1$, $A_2$ and $A_3$ substituents may be further elaborated by known techniques such as, for example, hydrolysis of the CN group to form COOH or by reduction with common reducing agents (such as, for example, Raney nickel) to form a primary amine, thereby transforming the $A_1$, $A_2$ and $A_3$ substituents into ion-exchange moieties. Thus, the group from which $A_1$, $A_2$ and $A_3$ are selected may further consist of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls), and the resulting polymeric compositions may thus comprise the sulfonyl fluoride moiety and one or more type of ion-exchange moiety, and may also comprise both cation-exchange and anion-exchange moieties.

Polymeric compositions of the present invention further include:

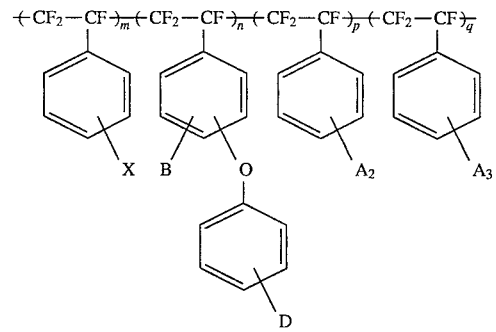

where n is an integer greater than zero, and m, p and q are zero or an integer greater than zero; $A_2$ and $A_3$ are selected from the group consisting of hydrogen, halogens, alkyls, perfluoroalkyls, CF=$CF_2$, CN, $NO_2$, OH, O—R (where R is selected from the group consisting of alkyls, perfluoroalkyls and aryls); X, B and D are selected from the group consisting of $SO_2F$, $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls); and the group from which D is selected further consists of hydrogen, and when m is also an integer greater than zero and X is $SO_2F$, the group from which B is selected further consists of hydrogen. The group from which $A_2$ and $A_3$ are selected may further consist of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls). The resulting polymeric compositions may thus comprise homopolymers and copolymeric compositions, and may also comprise polymeric compositions in which there is more than one ion-exchange moiety attached to a monomer fragment.

The substituents on the aromatic rings ($SO_2F$, $A_1$, $A_2$, $A_3$, X, B and D) may each be located in the ortho, meta or para positions, as indicated in the formulas wherein the chemical bond drawn for these substituents intersects the aromatic ring. Copolymeric compositions of the present invention may be binary, ternary or quaternary.

The polymeric compositions of the present invention can also consist essentially of the above chemical units. Thus, the polymers could include amounts of other monomers such as, for example, styrene.

Cross-linking is preferably introduced into the polymeric compositions of the present invention for applications in which it is, for example, desirable to increase dimensional stability, reduce swelling, modify the mechanical properties, or control ion-exchange selectivity.

In accordance with convention in the art, the above chemical formulas for polymeric compositions containing more than two monomers (where at least three of m, n, p, q are greater than zero) are intended to indicate that the monomers are present in the polymeric composition, but are not limited to the particular order in which the monomers are set forth in each general formula. For example, random linear copolymers and/or linear block copolymers formed from the indicated monomers are both contemplated.

The polymeric compositions of the present invention are suitably formed into membranes, and are preferably employed as ion-exchange membranes, most preferably as cation exchange membranes in electrochemical fuel cells.

DETAILED DESCRIPTION OF THE PREFERRED EMBODIMENTS

The polymeric compositions of the present invention are derived from copolymers of α,β,β-trifluorostyrene with a variety of substituted α,β,β-trifluorostyrenes.

In one aspect, a polymeric composition of the present invention includes:

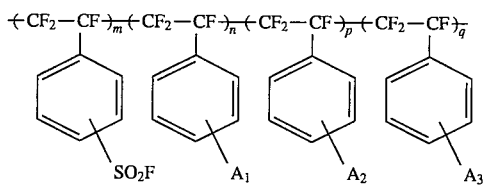

where m is an integer greater than zero, and n, p and q are zero or an integer greater than zero; $A_1$, $A_2$ and $A_3$ are selected from the group consisting of hydrogen, halogens, alkyls, perfluoroalkyls, CF=$CF_2$, CN, $NO_2$, OH, O—R (where R is selected from the group consisting of alkyls, perfluoroalkyls and aryls).

The polymeric compositions are produced by polymerization of a monomer having the chemical formula:

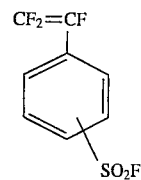

In the embodiment where only m is an integer greater than zero, the resulting polymeric composition is homopolymeric. In the embodiment where m is an integer greater than zero and at least one of n, p and q is an integer greater than zero, the resulting polymeric composition is copolymeric. For copolymeric compositions, the above sulfonyl fluoride-α,β,β-trifluorostyrene monomer is reacted with other monomers selected from the group of substituted α,β,β-trifluorostyrenes having the chemical formula:

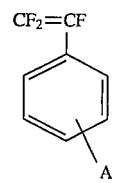

where A is selected from the group consisting of hydrogen, halogens, alkyls, perfluoroalkyls, CF=$CF_2$, CN, $NO_2$, OH, O—R (where R is selected from the group consisting of alkyls, perfluoroalkyls and aryls).

In a preferred method, the above monomers are mixed in an aqueous medium containing a free radical initiator and an emulsifying agent, at temperatures in the range of about 35° C.–100° C., and preferably in the range of 45° C.–65° C., for a time period of about 24 to 74 hours under an inert atmosphere. In general, the polymerization procedures and techniques employed in the preparation of polymeric compositions of the present invention are known. A suitable reference for polymerization techniques is *Textbook Of Polymer Science*, 3rd Edition, by F. W. Billmeyer, Jr., published by John Wiley & Sons.

In a further embodiment of a polymeric composition of the above formula, m is an integer greater than zero, and at least one of n, p and q is an integer greater than zero; the group from which $A_1$, $A_2$ and $A_3$ are selected further consists of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls). The resulting polymeric compositions may thus comprise the sulfonyl fluoride moiety and one or more type of ion-exchange moiety, and may also comprise both cation-exchange and anion-exchange moieties.

In an alternative aspect, a polymeric composition of the present invention includes:

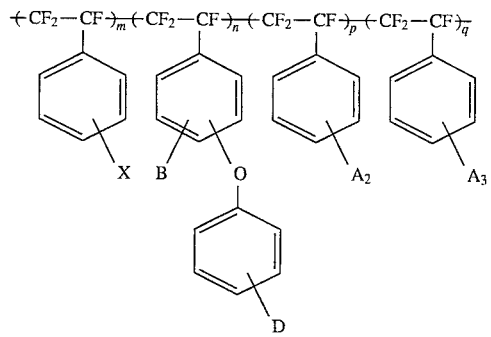

In one embodiment of this alternative aspect, m and n are integers greater than zero, p and q are zero or an integer greater than zero; X is $SO_2F$; $A_2$ and $A_3$ are selected from the group consisting of hydrogen, halogens, alkyls, perfluoroalkyls, $CF=CF_2$, CN, $NO_2$, OH, O—R (where R is selected from the group consisting of alkyls, perfluoroalkyls and aryls); B and D are selected from the group consisting of hydrogen, $SO_2F$, $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls). In a further embodiment, where m and n are integers greater than zero, and at least one of p and q is an integer greater than zero, the group from which $A_2$ and $A_3$ are selected further consists of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls).

In a still further embodiment of a polymeric composition of the above formula, n is an integer greater than zero, and m, p and q are zero or an integer greater than zero; $A_2$ and $A_3$ are selected from the group consisting of hydrogen, halogens, alkyls, perfluoroalkyls, $CF=CF_2$, CN, $NO_2$, OH, O—R (where R is selected from the group consisting of alkyls and perfluoroalkyls); X is selected from the group consisting of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls); B is selected from the group consisting of $SO_2F$, $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls); D is selected from the group consisting of hydrogen, $SO_2F$, $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls). The resulting polymeric compositions may thus comprise homopolymers or copolymers. In a further embodiment, where m and n are integers greater than zero, and at least one of p and q is an integer greater than zero, the group from which $A_2$ and $A_3$ are selected further consists of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls).

Ion-exchange moieties can be introduced into copolymers containing unsubstituted α,β, β-trifluorostyrene units (so-called "base copolymers") via aromatic substitution of at least a portion of those units. For example, base copolymers incorporating pendant unsubstituted phenyl rings can be sulfonated, phosphorylated, carboxylated, quaternary-aminoalkylated or chloromethylated, and further modified to include —$CH_2PO_3H_2$, —$CH_2NR_3^+$ where R is an alkyl, or —$CH_2NAr_3^+$ where Ar is a substituted or unsubstituted aromatic group, and other substituents, to provide a cation-exchange or anion-exchange polymeric materials. Further still, the pendent phenyl moiety may contain a hydroxyl group which can be elaborated by known methods to generate —$OSO_3H$, —$OPO_2H_2$ and —$OPO_3H_2$ cationic exchange sites on the polymer.

In a typical sulfonation reaction used to produce a cationic exchange membrane, the copolymer is dissolved in an appropriate solvent and then reacted with a sulfonating reagent, such as chlorosulfonic acid or a Lewis acid-base complex of sulfur trioxide. The solvent for such a reaction can be selected from the class consisting of chlorinated aliphatic hydrocarbons, such as dichloroethane, tetrachloroethylene and chloroform. The copolymer solution is rendered completely homogeneous prior to the addition of the solution containing the sulfonating reagent. The reaction is then run within the temperature range from about 10° C. up to the boiling point of the solvent or preferably in the range of 18° C.–40° C. To ensure adequate functionalization of the copolymer, the reaction is allowed to continue for a period of about one to about four hours, or longer dependent on the reaction temperature.

Copolymers containing sulfonyl fluoride moiety (—$SO_2F$) can be hydrolyzed to generate —$SO_3H$ cationic exchange sites on the polymer. In a typical hydrolysis reaction, the sulfonyl fluoride is converted to the free sulfonic acid functionality by hydrolysis in concentrated aqueous alkali metal hydroxide at elevated temperatures. This and other procedures for the hydrolysis of —$SO_2F$ to —$SO_3H$ are well-known to those skilled in the art. The latter approach to the introduction of —$SO_3H$ moieties offers advantages over sulfonation of a base copolymer. For example, it permits greater control over the ion-exchange capacity of the resultant polymer, and hydrolysis is a simpler reaction procedurally than aromatic substitution. In the process typically used for aromatic sulfonation, precipitation of the ionomer prior to reaction of all the available reactive pendant phenyl rings can lead to lower than preferable ion-exchange capacities in the product. Further, this process necessitates an additional purification step prior to membrane preparation. Copolymers containing —$SO_2F$ moieties, and no ion-exchange moieties, can be solvent cast or preferably extruded to produce membranes. The resultant membranes can be readily hydrolyzed to give sulfonated membranes as described previously. Extrusion, a method preferable for large-scale membrane production, is further facilitated by the lower glass transition temperatures typical of non-ionomeric copolymers.

Preferred polymeric compositions of the present invention include:

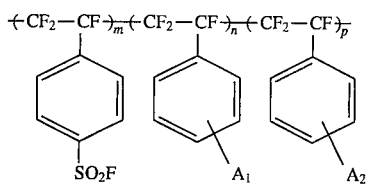

where m, n and p are integers greater than zero and $A_1$ and $A_2$ are selected from the group consisting of hydrogen, fluorine, $CF_3$, and para-phenoxy. These compositions can be converted into compositions incorporating ion-exchange moieties using techniques elaborated above.

As used herein, the term "aryl" refers to a substituted or unsubstituted aromatic group.

The substituents on the aromatic rings ($SO_2F$, $A_1$, $A_2$, $A_3$, X, B and D) in the embodiments described above may be located in the ortho, meta or para positions. In preferred aspects of the described embodiments, the substituents are in the meta or para positions.

The copolymers thus prepared possess favorable properties, such as thermal stability, chemical resistance and favorable mechanical properties, such as tensile strength, compared to the homopolymeric material formed from α,β,β-trifluorostyrene (TFS) alone.

Crosslinking can be introduced using conventional techniques well-known to those skilled in the art, such as those employed in preparing divinylbenzene crosslinked polystyrene. Crosslinking, for example to enhance the mechanical and physical properties of the membrane material, can be introduced by reaction of appropriate groups, before or preferably after the claimed polymeric compositions are formed into membranes. Monomers with substituents on the pendant phenyl rings which are suitable for subsequent crosslinking can be introduced into the copolymer in controlled amounts, thereby permitting some control of the degree of crosslinking in the membrane.

The following examples are for purposes of illustration and are not intended to limit the invention. Example 1 describes the synthesis of the monomer, p-sulfonyl fluoride α,β, β-trifluorostyrene from iodobenzene. Example 2 describes the emulsion copolymerization of p-sulfonyl fluoride-α,β,β-trifluorostyrene, α,β,β-trifluorostyrene and m-trifluoromethyl-α,β,β-trifluorostyrene. Example 3 describes the emulsion copolymerization of p-phenoxy-α,β,β-trifluorostyrene, α,β,β-trifluorostyrene and m-trifluoromethyl-α,β, β-trifluorostyrene. Examples 4 and 5 describe generalized procedures which may be used to prepare the claimed polymeric compositions. Example 4 describes a typical emulsion polymerization reaction which can be used for one or more monomers (solid or liquid) to make a homopolymer or copolymer, respectively. Example 5 describes a typical hydrolysis procedure which may be used to convert —$SO_2F$ moieties to —$SO_3H$.

EXAMPLE 1 p-Sulfonyl fluoride-α,β,β-trifluorostyrene (a) p-Iodobenzenesulfonyl chloride is prepared according to the method described in P. Sanecki, Polish Journal of Chemistry, Vol.66, 101–110 (1992):

To a dry 5 L three-neck round-bottom flask fitted with mechanical stirring, heating mantle, water-cooled condenser with adapter hose connected to an HCl trap, 2 L addition funnel and inert gas inlet is added 2.5 L of chloroform and chlorosulfonic acid (503 g, 4.32 mol). The mixture is heated to a gentle reflux and a solution of iodobenzene (400 g; 1.96 mol) in 0.5 L of chloroform is added over a period of 1 hour, during which time the reaction mixture changes color from yellow to dark red-purple, with evolution of HCl. The reaction is heated for a further 1 hour at reflux. Analysis by GC indicates complete conversion to p-iodobenzenesulfonyl chloride. The reaction is worked-up by pouring the mixture into a 6 L separatory funnel, and discarding the lower, mostly mineral acid, layer. The organic layer is neutralized and dried over $MgSO_4$. Solvent evaporation affords p-iodobenzenesulfonyl chloride as a crude yellow solid; yield approximately 593 g (quantitative). The product may be further purified by distillation under high vacuum, if desired.

(b) p-Iodobenzenesulfonyl fluoride is prepared using a method similar to that described in U.S. Pat. No. 3,560,568 issued Feb. 2, 1971:

p-Iodobenzenesulfonyl chloride (593 g, 1.96 mol), prepared as described in Example 1(a) above, is dissolved in 2.5 L of acetone and placed in a 5 L three-neck round-bottom flask fitted with a heating mantle, mechanical stirring and a water-cooled condenser. Potassium fluoride (126 g, 2.17 mol) and about 25 mL of water is added and the reaction is heated at reflux for approximately 5 hours. On cooling, the reaction mass is filtered and the solvent removed to provide a crude solid, which on purification, by distillation under high vacuum, affords p-iodobenzenesulfonyl fluoride as a white solid; yield 504 g (90%).

(c) 1,1,2-Trifluoroethenyl zinc bromide bromotrifluoroethylene (106 g, 0.66 mol) in DMF, prepared according to the method described in P. L. Heinze and D. J. Burton, Journal of Organic Chemistry, Vol. 53, 2714–2720 (1988), is added to a 1 L, three-neck round-bottom flask fitted with water-cooled condenser and inert gas inlet. p-Iodobenzenesulfonyl fluoride (128.5 g, 0.45 mol) prepared as described in Example 1(ii), palladium(0) bis(dibenzylidene acetone) (1.60 g, 2.8 mmol) and triphenylphosphine (1.86 g, 7.1 mmol) were added and the reaction is heated slowly to about 55° C. at which point the heat generated by the reaction is used to maintain the temperature at no higher than about 100° C. (cooling provided by an ice water bath). When the exotherm has subsided, the cooling bath is removed and external heating used to maintain the reaction at 75° C. for 3 hours. The reaction is then flash distilled under high vacuum (<1 mm Hg), isolating greater than 90% of the liquid components. The distillate is poured into a 2 L separatory funnel containing 1 L of deionized water. The products in the separatory funnel were then extracted with pentane (3×250 mL). The pentane extracts were combined, washed with water (3×250 mL), dried over anhydrous $MgSO_4$, filtered and evaporated to leave a clear yellow viscous liquid. The crude product is distilled under high vacuum to yield the title compound, p-sulfonyl fluoride-α, β,β-trifluorostyrene, (74.8 g, 69%) as a clear, pale yellow liquid. Infrared data in accord.

EXAMPLE 2

Emulsion copolymerization of p-sulfonyl
fluoride-α,β,β-trifluorostyrene,
m-trifluoromethyl-α,β,β-trifluorostyrene and
α,β,β-trifluorostyrene To a 1 L three-neck flask, fitted with a water-cooled condenser, inert gas inlet and thermocouple, is added 350 mL of nitrogen-degassed water, dodecylamine hydrochloride (6.80 g, 27 mmol) and the following monomers: α,β,β-trifluorostyrene (13.3 g, 85 mmol), m-trifluoromethyl-α,β,β-trifluorostyrene (9.90 g, 85 mmol) and p-sulfonyl fluoride-α,β,β-trifluorostyrene (40 g, 0.167 mole). The initiator, potassium persulfate (0.52 g, 1.8 mmol) is added and the reaction temperature elevated to 50° C. and held at this temperature for approximately 72 hours. Initial work-up of the reaction affords a yellow powder; yield 63.1 g (quantitative), intrinsic viscosity [η]=1.79 dL/g as determined in toluene at 30° C. $^{19}$F-NMR analysis performed on a VARIAN XL-300 NMR instrument using $CDCl_3$ as solvent is used to confirm incorporation of all three monomer fragments.

EXAMPLE 3

Emulsion copolymerization of
p-phenoxy-α,β,β-trifluorostyrene,
α,β,β-trifluorostyrene and
m-trifluoromethyl-α,β,β-trifluorostyrene To a 500 mL three-neck flask, fitted with a water-cooled condenser, inert gas inlet and thermocouple, is added 350 mL of nitrogen-degassed water, dodecylamine hydrochloride (4.57 g, 21 mmol) and the following monomers: α,β,β-trifluorostyrene (4.57 g, 30 mmol), m-trifluoromethyl-α,β,β-trifluorostyrene (6.76 g, 30 mmol), p-phenoxy-α,β,β-trifluorostyrene (22.44 g, 90 mmol). The initiator, potassium persulfate (0.39 g, 1.4 mmol) is then added and the reaction temperature elevated to 50° C. and held at this temperature for approximately 72 hours. Work-up of the reaction affords a pale yellow powder; yield 25.5 g (75%).

EXAMPLE 4

General Emulsion Copolymerization Procedure

To a 12 L reaction vessel equipped with a stirrer, water-cooled condenser, heating mantle and temperature controller is added 3.2 L of water. The water is degassed with nitrogen for approximately one hour and the reaction is kept under a nitrogen atmosphere throughout. Dodecylamine hydrochloride (58 g, 0.26 mol) is added and stirred into the water. At this point the desired monomers (which may be pre-mixed) are added to the vessel with stirring, to form an emulsion. The temperature of the emulsion is increased to 50° C. and potassium persulfate (4.42 g 15 mmol) is added. The reaction is allowed to continue for approximately 72 hours. Subsequently, 2 L of water is added to dilute the emulsion, followed by a solution of potassium hydroxide (80 g, 1.43 mol) dissolved in 2 L of water. The precipitated polymer is then stirred vigorously for up to one hour at 75° C. The mixture upon cooling is filtered, the filter cake being washed several times with fresh water. Having removed the majority of the filtrate, the cake is then transferred into a Soxhlet thimble and washed by continuous extraction with refluxing methanol to give a random, linear copolymer of the monomers introduced. The resultant product (typically an off-white powder) is sufficiently pure for further elaboration.

EXAMPLE 5

General Hydrolysis Procedure

The polymer, preferably in the form of a membrane, is treated with an excess of 6N aqueous potassium hydroxide at 80° C. for approximately 18 hours. The polymer is then washed with deionized water to remove unreacted potassium hydroxide and potassium fluoride by-product.

Copolymers prepared from monomer mixtures including sulfonyl fluoride-α,β,β-trifluorostyrene are produced in yields greater than 80% and are converted essentially quantitatively to the corresponding sulfonic acid analogues by hydrolysis.

While particular elements, embodiments and applications of the present invention have been shown and described, it will be understood, of course, that the invention is not limited thereto since modifications may be made by those skilled in the art, particularly in light of the foregoing teachings. It is therefore contemplated by the appended claims to cover such modifications as incorporate those features which come within the spirit and scope of the invention.

What is claimed is:

1. A polymeric composition comprising:

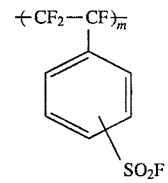

where m is an integer greater than zero.

2. A polymeric composition comprising:

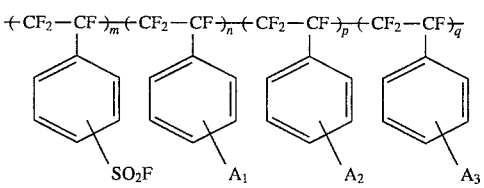

where m is an integer greater than zero, and at least one of n, p and q is an integer greater than zero; and $A_1$, $A_2$ and $A_3$ are selected from the group consisting of hydrogen, halogens, alkyls, perfluoroalkyls, $CF=CF_2$, CN, $NO_2$, OH, O—R (where R is selected from the group consisting of alkyls, perfluoroalkyls and aryls).

3. The polymeric composition of claim 2 wherein the group from which $A_1$, $A_2$ and $A_3$ are selected further consists of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls), and at least one of $A_1$, $A_2$ and $A_3$ is selected from the group consisting of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls).

4. A polymeric composition comprising:

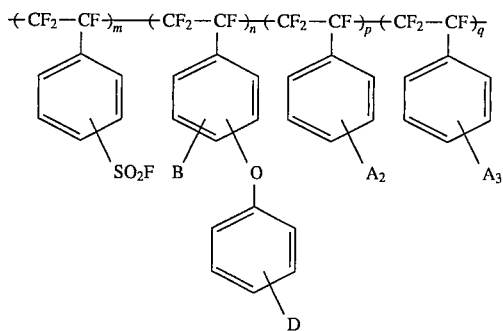

where m and n are integers greater than zero, p and q are zero or an integer greater than zero; $A_2$ and $A_3$ are selected from the group consisting of hydrogen, halogens, alkyls, perfluoroalkyls, $CF=CF_2$, CN, $NO_2$, OH, O—R (where R is selected from the group consisting of alkyls, perfluoroalkyls and aryls); and B and D are selected from the group consisting of hydrogen, $SO_2F$, $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls).

5. The polymeric composition of claim 4 wherein at least one of p and q is an integer greater than zero and wherein the group from which $A_2$ and $A_3$ are selected further consists of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls), and at least one of $A_2$ and $A_3$ is selected from the group consisting of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls).

6. A polymeric composition comprising:

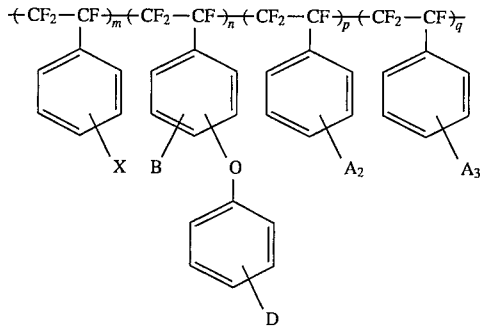

where n is an integer greater than zero, and m, p and q are zero or an integer greater than zero; $A_2$ and $A_3$ are selected from the group consisting of hydrogen, halogens, alkyls, perfluoroalkyls, $CF=CF_2$, CN, $NO_2$, OH, O—R (where R is selected from the group consisting of alkyls, perfluoroalkyls and aryls); X is selected from the group consisting of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls); B is selected from the group consisting of $SO_2F$, $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls); and D is selected from the group consisting of hydrogen, $SO_2F$, $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls).

7. The polymeric composition of claim 6 wherein the group from which $A_2$ and $A_3$ are selected further consists of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls), and at least one of $A_2$ and $A_3$ is selected from the group consisting of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls).

8. A polymeric composition according to any of claims 1–7 wherein the composition is at least partially crosslinked.

9. A polymeric composition consisting essentially of:

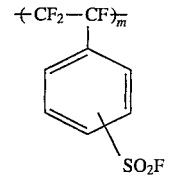

where m is an integer greater than zero.

10. A polymeric composition consisting essentially of:

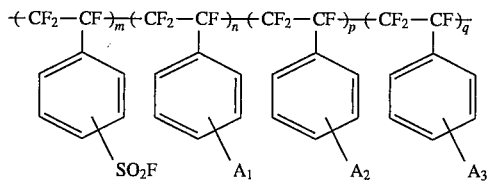

where m is an integer greater than zero, and at least one of n, p and q is an integer greater than zero; $A_1$, $A_2$ and $A_3$ are selected from the group consisting of hydrogen, halogens, alkyls, perfluoroalkyls, $CF=CF_2$, CN, $NO_2$, OH, O—R (where R is selected from the group consisting of alkyls, perfluoroalkyls and aryls).

11. The polymeric composition of claim 10 wherein the group from which $A_1$, $A_2$ and $A_3$ are selected further consists of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls), and at least one of $A_1$, $A_2$ and $A_3$ is selected from the group consisting of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls).

12. A polymeric composition consisting essentially of:

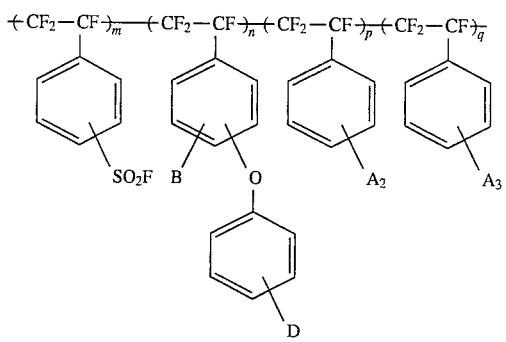

where m and n are integers greater than zero, p and q are zero or an integer greater than zero; $A_2$ and $A_3$ are selected from the group consisting of hydrogen, halogens, alkyls, perfluoroalkyls, $CF=CF_2$, CN, $NO_2$, OH, O—R (where R is selected from the group consisting of alkyls, perfluoroalkyls and aryls); B and D are selected from the group consisting of hydrogen, $SO_2F$, $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls).

13. The polymeric composition of claim 12 wherein at least one of p and q is an integer greater than zero and wherein the group from which $A_2$ and $A_3$ are selected further consists of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls), and at least one of $A_2$ and $A_3$ is selected from the group consisting of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls).

14. A polymeric composition consisting essentially of:

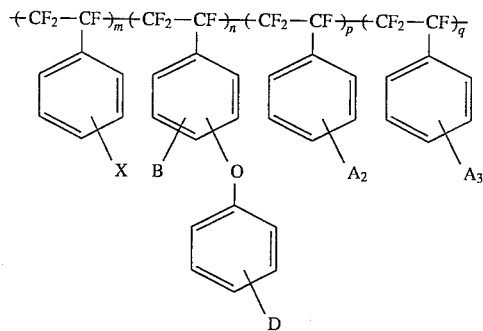

where n is an integer greater than zero, and m, p and q are zero or an integer greater than zero; $A_2$ and $A_3$ are selected from the group consisting of hydrogen, halogens, alkyls, perfluoroalkyls, $CF=CF_2$, CN, $NO_2$, OH, O—R (where R is selected from the group consisting of alkyls, perfluoroalkyls and aryls); X is selected from the group consisting of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls); B is selected from the group consisting of $SO_2F$, $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls); D is selected from the group consisting of hydrogen, $SO_2F$, $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls).

15. The polymeric composition of claim 14 wherein the group from which $A_2$ and $A_3$ are selected further consists of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls), and at least one of $A_2$ and $A_3$ is selected from the group consisting of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls).

16. A polymeric composition according to any of claims 9–15 wherein the composition is at least partially crosslinked.

17. A polymeric membrane comprising the polymeric composition according to any of claims 1–7 or 9–15.

18. A polymeric membrane consisting essentially of the polymeric composition according to any of claims 1–7 or 9–15.

19. An ion exchange membrane comprising the polymeric composition of claim 3.

20. An ion exchange membrane comprising the polymeric composition of claim 4, wherein either or both of B and D is not hydrogen or $SO_2F$.

21. An ion exchange membrane comprising the polymeric composition of claim 5.

22. An ion exchange membrane comprising the polymeric composition of claim 6, wherein m is greater than zero or the group from which B is selected excludes $SO_2F$ or the group from which D is selected excludes hydrogen and $SO_2F$.

23. An ion exchange membrane comprising the polymeric composition of claim 7.

24. An ion exchange membrane according to any of claims 19–23, wherein the composition is at least partially crosslinked.

25. An electrochemical fuel cell comprising the ion exchange membrane according to any of claims 19–23.

26. An ion exchange membrane comprising the polymeric composition of claim 11.

27. An ion exchange membrane comprising the polymeric composition of claim 12, wherein either or both of B and D is not hydrogen or $SO_2F$.

28. An ion exchange membrane comprising the polymeric composition of claim 13.

29. An ion exchange membrane comprising the polymeric composition of claim 14, wherein m is greater than zero or the group from which B is selected excludes $SO_2F$ or the group from which D is selected excludes hydrogen and $SO_2F$.

30. An ion exchange membrane comprising the polymeric composition of claim 15.

31. An ion exchange membrane according to any of claims 26–30, wherein the composition is at least partially crosslinked.

32. An electrochemical fuel cell comprising the ion exchange membrane according to any of claims 26–30.

33. A polymeric composition comprising:

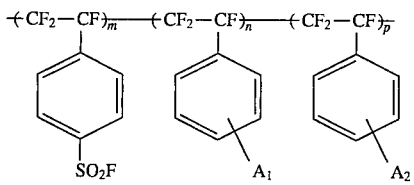

where m, n and p are integers greater than zero and $A_1$ and $A_2$ are selected from the group consisting of hydrogen, fluorine, $CF_3$, and para-phenoxy.

34. A polymeric composition consisting essentially of:

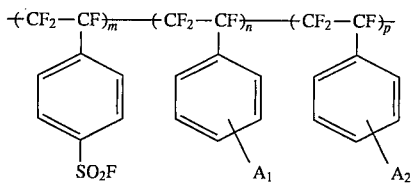

where m, n and p are integers greater than zero and $A_1$ and $A_2$ are selected from the group consisting of hydrogen, fluorine, $CF_3$, and para-phenoxy.

35. A method of preparing an ion exchange membrane comprising hydrolyzing at least a portion of the $SO_2F$ moieties in the polymer composition of claims 33 and 34.

36. A homopolymer of

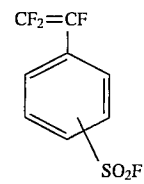

37. The homopolymer according to claim 31 wherein the homopolymer is at least partially crosslinked.

38. A polymeric membrane comprising the homopolymer according to claim 31.

39. A polymeric membrane consisting essentially of the homopolymer according to claim 31.

40. A polymeric membrane comprising the polymeric composition according to claim 8.

41. A polymeric membrane comprising the polymeric composition according to claim 16.

42. A polymeric membrane consisting essentially of the polymeric composition according to claim 8.

43. A polymeric membrane consisting essentially of the polymeric composition according to claim 16.

44. An electrochemical fuel cell comprising the ion exchange membrane according to claim 24.

45. An electrochemical fuel cell comprising the ion exchange membrane according to claim 31.

* * * * *